though the invention is described in connection with

United States Patent [19]
Hyson

[11] 3,975,518
[45] Aug. 17, 1976

[54] LIQUID WATER-SOLUBLE INSECTICIDAL CONCENTRATES OF S-METHYL N-[(METHYLCARBAMOYL)-OXY]THIOACETIMIDATE

[75] Inventor: Archibald Miller Hyson, Newark, Del.

[73] Assignee: E. I. Du Pont de Nemours and Company, Wilmington, Del.

[22] Filed: Apr. 10, 1974

[21] Appl. No.: 459,579

Related U.S. Application Data

[63] Continuation-in-part of Ser. No. 359,503, May 11, 1973, abandoned.

[52] U.S. Cl. .............................. 424/173; 252/364; 424/298; 424/300; 424/327
[51] Int. Cl.² ...................... A01N 9/12; A01N 9/20
[58] Field of Search ............ 252/364; 424/173, 327, 424/298, 300

[56] References Cited
UNITED STATES PATENTS

| | | | |
|---|---|---|---|
| 3,576,834 | 4/1971 | Buchanan | 260/453 |
| 3,639,633 | 2/1972 | Buchanan | 424/327 |
| 3,647,861 | 3/1972 | Buchanan | 260/481 R |

OTHER PUBLICATIONS

The Merck Index of Chemicals & Drugs (1960) p. 310.

Primary Examiner—Leonard Schenkman
Assistant Examiner—Allen J. Robinson

[57] ABSTRACT

Ternary and quaternary solvent systems consisting essentially of 20% to 92% by weight cyclohexanone, 3% to 25% by weight lower alkanol, and at least 5% by weight water, wherein 0–65% of said cyclohexanone can be replaced by an equal quantity of cyclohexanol, such that when sufficient S-methyl N-[(methylcarbamoyl)oxy]thioacetimidate to create a 35% solution of said thioacetimidate is dissolved therein at 25°C., a single phase results, and single phase, liquid, water-soluble insecticidal concentrates of S-methyl N-[(methylcarbamoyl)oxy]thioacetimidate containing 15% to 35% by weight of said thioacetimidate in such a ternary or quaternary solvent system.

7 Claims, 2 Drawing Figures

LIQUID WATER-SOLUBLE INSECTICIDAL CONCENTRATES OF S-METHYL N-[(METHYLCARBAMOYL)-OXY]THIOACETIMIDATE

CROSS-REFERENCE TO RELATED APPLICATIONS

This is a continuation-in-part of U.S. Patent application Ser. No. 359,503, filed May 11, 1973 now abandoned.

BACKGROUND OF THE INVENTION

Insecticidal compositions exist in a wide variety of formulations. Liquid formulations are among the most useful of these since they are convenient to handle, easily measured, quick to disperse in water, and lend themselves to low-volume applications. Liquid formulations eliminate the toxic dust problem normally associated with dry formulations. As compared to conventional solid formulations they are easier to dilute to spray volume. Liquid concentrates can be pumped; and even when used in small amounts, liquid formulations can be more conveniently and accurately measured than solid formulations.

The active insecticidal ingredient, S-methyl N-[(methylcarbamoyl)oxy]thioacetimidate, a method of making it, and a wide variety of formulations and methods for using it are disclosed in U.S. Pat. No. 3,647,861, issued Mar. 7, 1972, to James B. Buchanan. Related disclosures are found in U.S. Pat. Nos. 3,639,633 and 3,576,834 issued Feb. 1, 1972, and Apr. 27, 1971, respectively to James B. Buchanan. Included is an insecticidal composition containing 25% by weight S-methyl N-[(methylcarbamoyl)oxy]thioacetimidate dissolved in a solvent consisting of 60% by weight methanol and 40% by weight water. (In the description which follows all percents are by weight.)

Compositions containing said thioacetimidate are frequently subjected to near freezing or sub-freezing temperatures during transit or storage. When the composition is in the form of a liquid concentrate, low temperature solubility then becomes an important consideration in choosing a particular solvent system. The above-mentioned 60:40 methanol:water solvent possesses relatively low solubility for said thioacetimidate at low temperatures. For example, the solubility of said thioacetimidate in said solvent system is less than 18% at 0°C. and less than 15% at −6°C.

Copending U.S. Pat. application Ser. No. 317,802, filed Dec. 22, 1972 now U.S. Pat. No. 3,862,316, by Johnny Leroy Armstrong discloses liquid, water-soluble concentrated compositions of S-methyl N-[(methylcarbamoyl)oxy]thioacetimidate containing 20% to 30% of said thioacetimidate dissolved in a binary solvent consisting essentially of 80% to 95% methanol and 5% to 20% water. Such a composition gives an unexpected increase in the low temperature solubility of said thioacetimidate, but the proportion of methanol necessary to cause this desired increase in low temperature solubility will also cause the resulting composition to possess a relatively low flash point. Thus, handling of such a composition will require precautions, and a certain amount of inconvenience will result.

It would, of course, be desirable to maintain or increase the low temperature solubility while reducing the flammability hazard (i.e., increasing the flash point). Preferably, it would be desirable to maintain or increase the low temperature solubility while increasing the flash point to at least 100°F. to provide a minimum flammability hazard and to eliminate the necessity for special precautions and inconvenience in handling.

Thus, a number of criteria become important in the selection of the solvent system for use in the preparation of liquid, water-soluble concentrates of S-methyl N-[(methylcarbamoyl)oxy]thioacetimidate. The thioacetimidate must have a high level of low temperature solubility in the chosen solvent system. The solvent system should have a relatively high flash point. The solvent system when admixed with the thioacetimidate must provide a homogeneous (i.e., single phase) composition. In addition, the solvent system must be safe with respect to the plants that are to be treated with the thioacetimidate composition, i.e., the solvent cannot be phytotoxic. Furthermore, the solvents must be approved by the Environmental Protection Agency for use on growing crops.

It has now been found unexpectedly that each of the above-mentioned criteria can be satisfied by the ternary and quaternary solvent systems of the present invention. In particular, it has been found unexpectedly that when sufficient S-methyl N-[(methylcarbamoyl)oxy]thioacetimidate to create a 15% to 35% solution of said thioacetimidate is dissolved in the ternary or quaternary solvent systems of the present invention at 25°C. there will result a homogeneous (single phase) composition, i.e., the dissolution of said thioacetimidate in the solvent system of the present invention aids in the formation of a single phase. It has further been found that said thioacetimidate possesses an unexpectedly high level of low temperature solubility in the solvent systems of the present invention.

SUMMARY OF THE INVENTION

This invention comprises improved solvent systems for use in the preparation of liquid water-soluble concentrates of S-methyl N-[(methylcarbamoyl)oxy]thioacetimidate and improved compositions containing 15% to 35% of said thioacetimidate dissolved in the improved solvent systems of the present invention.

The improved solvent systems consist essentially of 20% to 92% cyclohexanone, 3% to 25% lower alkanol, and at least 5% water, wherein 0–65% of said cyclohexanone is replaced by an equal quantity of cyclohexanol, such that when sufficient S-methyl N-[(methylcarbamoyl)oxy]thioacetimidate to create a 35% solution of said thioacetimidate is dissolved in said solvent systems at 25°C., a single phase results. The lower alkanol is preferably methanol, but the solvent system can contain up to about 10% of other alkanols, such as ethanol, isopropanol, and n-propanol in lieu of or in admixture with said methanol. The quantity of cyclohexanone replaced by cyclohexanol is preferably 40–65%, by weight, and most preferably 54–62%.

The improved compositions of the present invention comprises those single phase, liquid, water-soluble compositions which result when sufficient S-methyl N-[(methylcarbamoyl)oxy]thioacetimidate to create a 15% to 35% solution of said thioacetimidate is dissolved in a ternary or quaternary solvent system of the present invention at 25°C. The improved compositions of the present invention can be made by direct dissolution of solid particulate S-methyl N-[(methylcarbamoyl)oxy]thioacetimidate and an appropriate quantity of the above-mentioned solvent system. A more convenient way, however, would be to bring into contact the required quantities of the above-mentioned solvent and the molten product which results from the process which is the subject matter of copending U.S. Pat. application Ser. No. 317,803, filed Dec. 22, 1972 now U.S. Pat. No. 3,855,260, by Robert J. Vollkommer. As pointed out therein so doing has the advantage of dissolving and cooling said thioacetimidate simultaneously. The resulting composition possesses a high flash point, and said thioacetimidate remains in solution at low temperatures.

DESCRIPTION OF THE FIGURES

The graphs shown in FIG. 1 represent the solubility of S-methyl N-[(methylcarbamoyl)oxy]thioacetimidate in each of three different ternary solvent systems as a function of temperature. The dashed line represents the solubility of said thioacetimidate in a solvent system consisting essentially of 55% butyl cellosolve, 15% methanol, and 30% water. The solid lines represent the solubility of said thioacetimidate in two different solvent systems within the scope of the present invention, the first being 60% cyclohexanone, 10% methanol, and 30% water, and the second being 70% cyclohexanone, 9% methanol, and 21% water.

The three-component cyclohexanone, methanol, and water solvent system is depicted graphically in FIG. 2, i.e., the solvent systems of the present invention are those that fall on or within the trapezoid DEFG which form a homogeneous (single phase) composition when sufficient S-methyl N[(methylcarbamoyl)oxy]thioacetimidate to create a 35% solution of said thioacetimidate is dissolved in said solvent system at 25°C. It is emphasized for the purpose of clarity that most, but not all, of the solvent systems represented by the area within trapezoid DEFG will result in a homogeneous (single phase) composition. Only those that do result in a single phase composition when admixed with sufficient thioacetimidate to create a 35% solution of said thioacetimidate in said solvent system at 25°C. are considered to be within the scope of the present invention. The solvent systems of the present invention that are preferred are those that fall on or within the parallelogram HIJK which form a homogeneous composition when sufficient thioacetimidate to create a 35% solution of said thioacetimidate is dissolved in said preferred solvent system at 25°C. The area of the graph to the left of the dashed line LM represents ternary solvent systems having a flash point greater than 100°F. Accordingly, the most preferred solvent systems of the present invention are those that fall on or within the parallelogram HIJK but to the left of the line LM.

Figure 1:
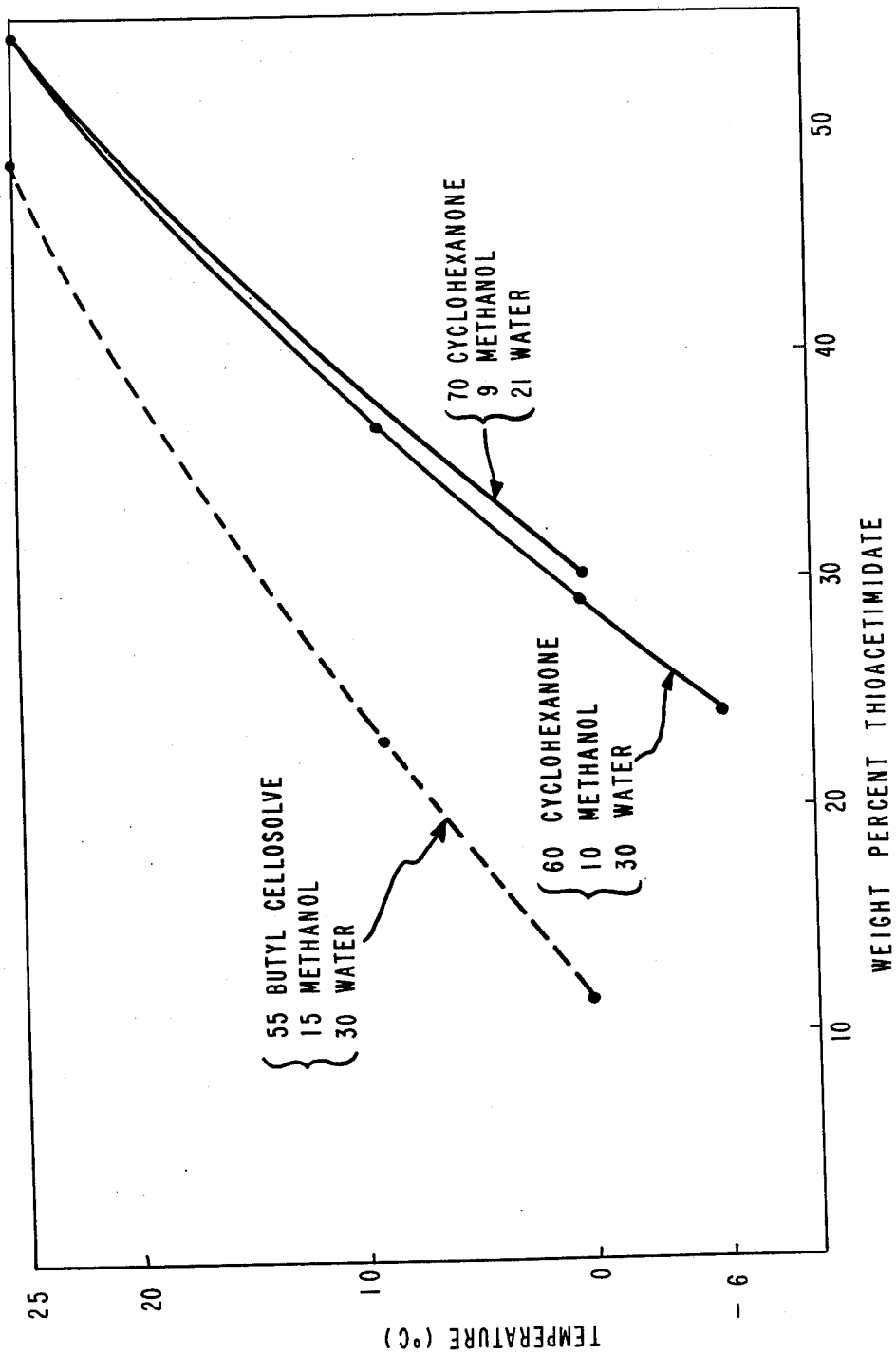
Figure 2:
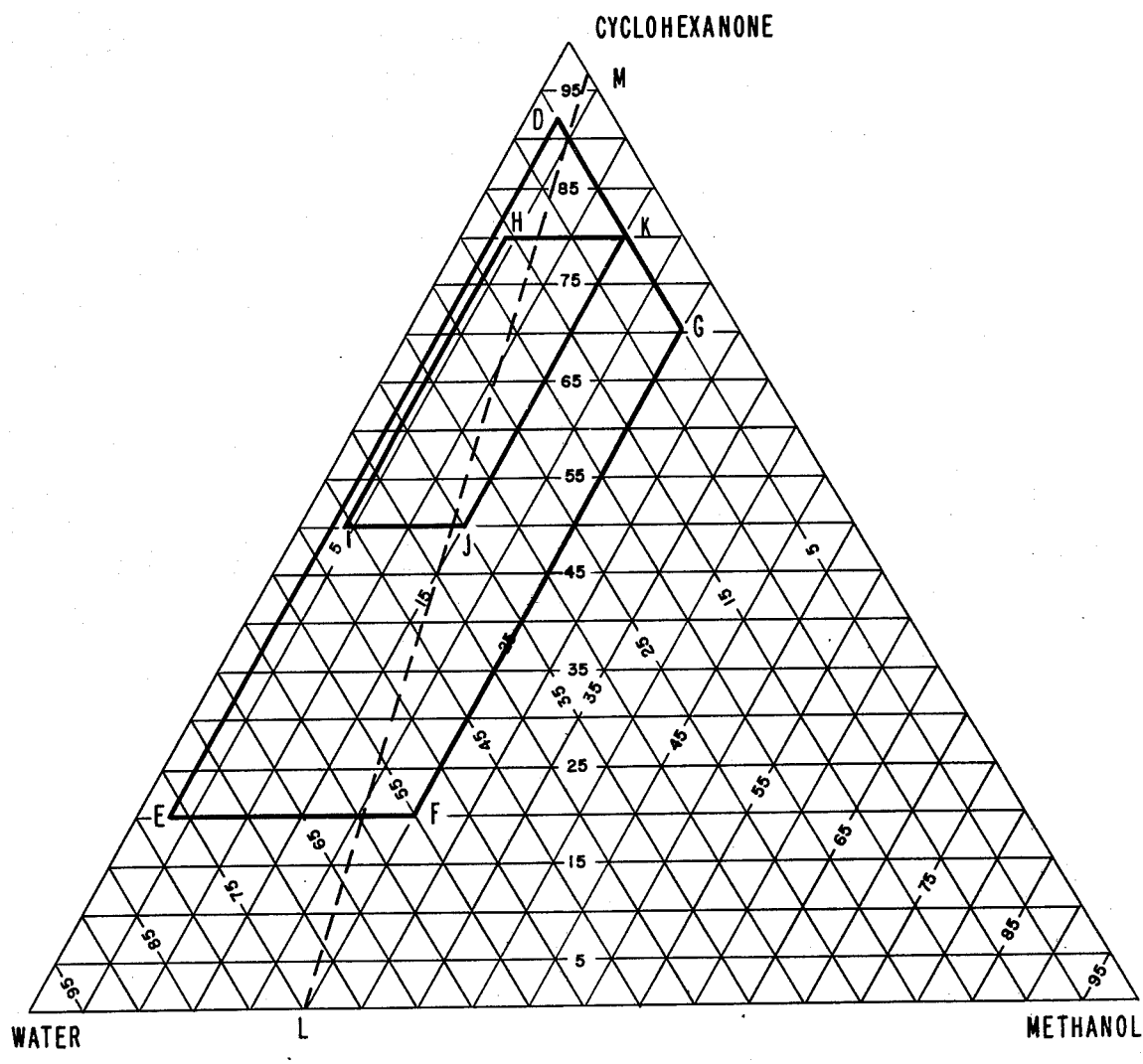

Similarly, the compositions of the present invention are those compositions formed when sufficient S-methyl N-[(methylcarbamoyl)oxy]thioacetimidate to create a 15% to 35% solution of said thioacetimidate is dissolved in solvent systems represented by the area bounded by trapezoid DEFG which are homogeneous at 25°C; preferred compositions of the present invention are those compositions formed when sufficient thioacetimidate to create a 15% to 35% solution of said thioacetimidate is dissolved in solvent systems represented by the area bounded by trapezoid HIJK which are homogeneous at 25°C.; and most preferred compositions of the present invention are those compositions formed when sufficient thioacetimidate to create a 15% to 35% solution of said thioacetimidate is dissolved in solvent systems represented by the area bounded by the parallelogram HIJK but to the left of line LM which are homogeneous at 25°C.

DETAILED DESCRIPTION OF THE INVENTION

The improved solvent system of the present invention consists essentially of 20% to 92% cyclohexanone, 3% to 25% lower alkanol, and at least 5% water, wherein 0–65% by weight of said cyclohexanone is replaced by an equal quantity of cyclohexanol, such that when sufficient S-methyl N-[(methylcarbamoyl)oxy]thioacetimidate to create a 35% solution of said thioacetimidate is dissolved in said solvent system at 25°C., a single phase results. Preferred solvent systems of the present invention are those that consist essentially of 50% to 80% cyclohexanone, 4% to 15% methanol, and at least 5% water, such that when sufficient thioacetimidate to create a 15% to 35% solution of said thioacetimidate is dissolved in said preferred solvent system at 25°C. a homogeneous composition results. More preferred solvent systems of the present invention are those that consist essentially of 50% to 80% cyclohexanone, 6% to 15% methanol, and at least 5% water. All of the said more preferred solvent systems will result in a single phase when sufficient S-methyl N-[(methylcarbamoyl)oxy]thioacetimidate to create a 15% to 35% solution of said thioacetimidate is dissolved therein. Especially preferred solvent systems are those more preferred solvent systems having a flash point greater than 100°F. The most preferred solvent systems consist essentially of 60% cyclohexanone, 10% to 15% methanol, and 25% to 35% water. It is understood that in these preferred solvent systems, as well, 0–65% of said cyclohexanone can be replaced by an equal amount of cyclohexanol, and further that the quantity of cyclohexanone so replaced is preferably 40% to 65%, by weight, and most preferably 54% to 62%.

The improved compositions of this invention comprise those liquid, water-soluble concentrates of S-methyl N-[(methylcarbamoyl)oxy]thioacetimidate which result when sufficient thioacetimidate to create a 15% to 35% solution of said thioacetimidate is dissolved in a solvent system consisting essentially of 20% to 92% cyclohexanone, 3% to 25% lower alkanol, and at least 5% water wherein 0–65% of said cyclohexanone, by weight, is replaced by an equal quantity of cyclohexanol, which are homogeneous at 25°C. Preferred compositions of the present invention include those liquid, water-soluble concentrates which result when sufficient thioacetimidate to create a 15% to 35% solution of said thioacetimidate is dissolved in a solvent system consisting essentially of 50% to 80% cyclohexanone, 4% to 15% methanol, and at least 5% water which are homogeneous at 25°C. More preferred compositions of the present invention comprise 15% to 35% solutions of said thioacetimidate in a solvent consisting essentially of 50% to 80% cyclohexanone, 6% to 15% methanol, and at least 5% water. Especially preferred compositions of the present invention comprise 15% to 35% solutions of said thioacetimidate in one of said above-mentioned especially preferred solvents. The most preferred compositions comprise a 15% to 35% solution of said thioacetimidate in the above-mentioned most preferred solvent systems.

The lower alkanol is preferably methanol, but the solvent system can contain up to about 10% of other lower alkanols such as ethanol, isopropanol, and n-propanol in lieu of or in admixture with said methanol.

As mentioned above in connection with the solvent systems, it is to be understood that in the preferred compositions of the present invention, as well, 0–65% of said cyclohexanone can be replaced by an equal amount of cyclohexanol and further that the quantity of cyclohexanone so replaced is preferably 40% to 65%, by weight, and most preferably 54% to 62%.

As mentioned above, the thioacetimidate possesses an unexpectedly high level of low temperature solubility in the solvent systems of the present invention. This facet of the present invention is demonstrated by the following comparison of the amount of said thioacetimidate that will dissolve in the corresponding amount of each of the three solvent components separately.

The solubility of said thioacetimidate in each of the three solvent components at 25°C. is shown in the table below:

| Solvent Component | % Solubility at 25°C. |
| --- | --- |
| Cyclohexanone | 28 |
| Methanol | 60 |
| Water | 6 |

Thus, in 60 parts of cyclohexanone one could dissolve 23.3 parts of said thioacetimidate; in 10 parts of methanol one could dissolve 15.0 parts of said thioacetimidate; and in 30 parts of water one could dissolve 1.9 parts of said thioacetimidate. This totals 40.2 parts of said thioacetimidate in 100 parts of solvent when the solvent components remain separate.

It has been found, however, that when the three solvent components are combined into a solvent system, a strong synergistic effect results. Thus, it has been found unexpectedly that at 25°C. 100 parts of a 60:10:30 cyclohexanone:methanol:water solvent system can dissolve 117.4 parts of said thioacetimidate, i.e., almost three times the amount that can be dissolved in comparable amounts of each of the solvent components separately.

Similarly, the solubility of said thioacetimidate in each of the three solvent components at 0°C. is shown in the table below:

| Solvent Component | % Solubility at °C. |
| --- | --- |
| Cyclohexanone | 14 |
| Methanol | 30 |
| Water | 3 |

Thus, at 0°C. in 60 parts of cyclohexanone one could dissolve 9.8 parts of said thioacetimidate; in 10 parts of methanol one could dissolve 4.3 parts of said thioacetimidate; and in 30 parts of water one could dissolve 0.9 part of said thioacetimidate. This totals 15.0 parts of said thioacetimidate in 100 parts of solvent when the solvent components remain separate.

It has been found, however, that when the three solvent components are combined into a solvent system, 100 parts of a 60:10:30 cyclohexanone:methanol:water solvent system can dissolve 40.8 parts of said thioacetimidate at 0°C., i.e., again almost three times that which can be dissolved in comparable amounts of each of the solvent components separately.

Further demonstration of the superior, low temperature solubility of said thioacetimidate in the cyclohexanone:methanol:water solvent systems of the present invention is provided by FIG. 1. For example, at 0°C. two solvent systems of the present invention are capable of dissolving 29% and 30%, respectively, of said thioacetimidate whereas the 55:15:30 butyl cellosolve:methanol:water solvent system is capable of dissolving only 12% of said thioacetimidate.

Compositions of the present invention can also contain minor amounts (i.e., from about 0.001% to 0.1% by weight) of coloring agent. Any coloring agent or combination of coloring agents that does not react chemically with the other ingredients of the compositions can be used. Suitable coloring agents include the sodium, calcium, and ammonium lignosulfates such as the "Marasperses", manufactured by the American Can Company, "Polyfons", manufactured by Westvaco Corporation, and "Lignosols", manufactured by Lignosol Chemicals (see McCutcheon's Detergents and Emulsifiers 1972 Annual, published 1972 by McCutcheon's Division, Allured Publishing Company) as well as organic dyes such as FD&C Blue No. 1, FD&C Red No. 3, or FD&C Yellow No. 5 (see The Food Chemical News Guide, published February 28, 1972, by Food Chemical News, Inc.). "Marasperse CB" and "FD&C Blue No. 1" are preferred.

The liquid, water-soluble concentrates of the present invention are effective against an enormous variety of pests as described in detail in the abovementioned U.S. Pat. No. 3,629,633, and may be diluted with water, methanol, or water/methanol mixtures. Broadly speaking, the active ingredient should normally be used at levels of about 0.05 kg/hectare to about 35 kg/hectare.

The following examples further illustrate the improved compositions of the present invention.

EXAMPLE 1

The following compositions were prepared by dissolving the S-methyl N-[(methylcarbamoyl)oxy]thioacetimidate in the ternary or quaternary solvent systems at ambient temperature.

| Sample | Percent Thioacetimidate | Cyclohexanone Ratio | Methanol Ratio | Ethanol Ratio | Isopropanol Ratio | Water Ratio | Temperature (°C) at which Freeze Stable | Closed Cup Flash Point °F. |
| --- | --- | --- | --- | --- | --- | --- | --- | --- |
| A | 24 | 60 | 10 | — | — | 30 | −6 | 102 |
| B | 24 | 60 | 8 | — | — | 32 | −6 | 106 |
| C | 24 | 55 | 10 | — | — | 35 | −6 | 103 |
| D | 24 | 50 | 15 | — | — | 35 | −6 | 94 |
| E | 34 | 70 | 9 | — | — | 21 | +4 | 102 |
| F | 15 | 75 | 15 | — | — | 10 | 0 | — |
| G | 24 | 60 | 25 | — | — | 15 | −6 | — |
| H | 24 | 30 | 15 | — | — | 55 | 0 | — |
| I | 24 | 85 | 5 | — | — | 10 | 0 | — |
| J | 24 | 65 | 4 | 5 | — | 26 | −6 | — |
| K | 24 | 60 | 8 | — | 3 | 29 | −6 | — |

-continued

| Sample | Percent Thioacetimidate | Cyclohexanone Ratio | Methanol Ratio | Ethanol Ratio | Isopropanol Ratio | Water Ratio | Temperature (°C) at which Freeze Stable | Closed Cup Flash Point °F. |
|---|---|---|---|---|---|---|---|---|
| L | 23 | 60[1] | 15 | — | — | 25 | 0 | 104 |

[1]approximately 57% of the cyclohexanone was replaced by an equal quantity of cyclohexanol.

EXAMPLE 2

Solubilities of S-methyl N-[(methylcarbamoyl)oxy]-thioacetimidate at −6°C., 0°C., and 25°C. in various cyclohexanone:methanol:water solvent systems were determined as follows. Solutions of said thioacetimidate in each of the various solvent systems containing excess thioacetimidate (i.e., more thioacetimidate than would remain in solution at equilibrium at each of the three above-mentioned temperatures) were prepared. These solutions were then slowly cooled to their designated temperatures, in effect, creating supersaturated solutions, and they were then seeded to initiate crystallization. After equilibrium had been reached, approximately 10 ml. of the supernatant was weighed and then evaporated to dryness. The remaining solids (thioacetimidate) were weighed and the weight percentage of said thioacetimidate soluble in the various solvent systems at the given temperatures were calculated.

| | Composition of Solvent (%) | | | Solubility in Solvent System (%) | | |
|---|---|---|---|---|---|---|
| Sample | Cyclohexanone | Methanol | Water | −6°C | 0°C | 25°C |
| 1 | 60 | 10 | 30 | 24.1 | 29.13 | 54.35 |
| 2 | 65 | 10 | 25 | — | 30.25 | 54.29 |
| 3 | 70 | 9 | 21 | — | 30.10 | 53.94 |
| 4 | 30 | 25 | 45 | — | 23.6 | 51.5 |
| 5 | 50 | 15 | 35 | — | 29.4 | 53.4 |
| 6 | 40 | 20 | 40 | — | 26.8 | 53.6 |

What is claimed is:

1. An insecticidal composition which is substantially homogeneous, has low-temperature stability and a high flash point which comprises an insecticidally effective amount of S-methyl N-[(methylcarbamoyl)oxy]thioacetimidate in a solvent system consisting essentially of 20–92% cyclohexanone, 3–25% lower alkanol and at least 5% water, wherein 0–65% by weight of said cyclohexanone is replaced by an equal quantity of cyclohexanol, such that when sufficient thioacetimidate to create 15–35% solution of said thioacetimidate is dissolved therein at 25°C, a single phase results.

2. The composition of claim 1 wherein said cyclohexanone is present in an amount of 50–80%, and said lower alkanol is present in an amount of 4–15% and 40–65% of said cyclohexanone is replaced by an equal quantity of cyclohexanol.

3. The composition of claim 1 wherein said lower alkanol is selected from the group consisting of methanol, ethanol and isopropanol.

4. The composition of claim 1 wherein said lower alkanol is methanol.

5. The composition of claim 2 wherein said lower alkanol is methanol.

6. The composition of claim 1 wherein said solvent system consists essentially of 50–80% cyclohexanone, 6–15% methanol and at least 5% water, wherein 40–65% of said cyclohexanone is replaced by an equal quantity of cyclohexanol.

7. The composition of claim 1 wherein said solvent system has a flash point greater than 100°F.

* * * * *